US012698283B2

(12) United States Patent
Gaddam

(10) Patent No.: US 12,698,283 B2
(45) Date of Patent: Aug. 4, 2026

(54) QUINOLINE DERIVATIVES, PHARMACEUTICALLY ACCEPTABLE SALTS, AND METHODS OF USE THEREOF

(71) Applicant: vTv Therapeutics LLC, High Point, NC (US)

(72) Inventor: Bapu Gaddam, Ellicott City, MD (US)

(73) Assignee: vTv Therapeutics LLC, High Point, NC (US)

( * ) Notice: Subject to any disclaimer, the term of this patent is extended or adjusted under 35 U.S.C. 154(b) by 652 days.

(21) Appl. No.: 18/003,758

(22) PCT Filed: Jul. 31, 2020

(86) PCT No.: PCT/US2020/044410
§ 371 (c)(1),
(2) Date: Dec. 29, 2022

(87) PCT Pub. No.: WO2022/005494
PCT Pub. Date: Jan. 6, 2022

(65) Prior Publication Data

US 2023/0265089 A1 Aug. 24, 2023

Related U.S. Application Data

(60) Provisional application No. 63/045,240, filed on Jun. 29, 2020.

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
See application file for complete search history.

(56) References Cited

U.S. PATENT DOCUMENTS

| | | | |
|---|---|---|---|
| 4,927,820 | A | 5/1990 | Shutske et al. |
| 5,834,485 | A | 11/1998 | Dyke et al. |
| 7,964,608 | B2 | 6/2011 | Mjalli et al. |
| 8,329,715 | B2 | 12/2012 | Mjalli et al. |
| 8,853,226 | B2 | 10/2014 | Mjalli et al. |
| 9,163,022 | B2 | 10/2015 | Mjalli et al. |
| 9,393,245 | B2 | 7/2016 | Mjalli et al. |
| 9,687,489 | B2 | 6/2017 | Mjalli et al. |
| 9,833,457 | B2 | 12/2017 | Mjalli et al. |
| 10,085,990 | B2 | 10/2018 | Mjalli et al. |
| 10,391,097 | B2 | 8/2019 | Mjalli et al. |
| 10,568,888 | B2 | 2/2020 | Mjalli et al. |
| 12,545,676 | B2 | 2/2026 | Gaddam et al. |
| 2003/0105129 | A1 | 6/2003 | Mortlock et al. |
| 2004/0171593 | A1 | 9/2004 | Keating et al. |
| 2005/0065116 | A1 | 3/2005 | Carson et al. |
| 2008/0255209 | A1 | 10/2008 | Klein et al. |
| 2009/0018333 | A1 | 1/2009 | Grauert et al. |
| 2010/0190808 | A1 | 7/2010 | Mjalli et al. |
| 2011/0160234 | A1 | 6/2011 | Mjalli et al. |
| 2012/0028932 | A1 | 2/2012 | Nickolaus et al. |
| 2012/0035143 | A1 | 2/2012 | Nickolaus et al. |
| 2018/0360839 | A1 | 12/2018 | Mjalli et al. |
| 2023/0312559 | A1 | 10/2023 | Gaddam et al. |

FOREIGN PATENT DOCUMENTS

| | | | |
|---|---|---|---|
| EP | 0143001 | A2 | 5/1985 |
| PL | 193012 | B1 | 1/2007 |
| WO | WO-9857936 | A1 | 12/1998 |
| WO | WO-03024489 | A2 | 3/2003 |
| WO | WO-03062238 | A1 | 7/2003 |
| WO | WO-2007004958 | A1 | 1/2007 |
| WO | WO-2009094528 | A1 | 7/2009 |
| WO | WO-2009125809 | A1 | 10/2009 |
| WO | WO-2011124524 | A1 | 10/2011 |
| WO | WO-2011124525 | A1 | 10/2011 |
| WO | WO-2022005494 | A1 | 1/2022 |
| WO | WO-2022026350 | A1 | 2/2022 |

OTHER PUBLICATIONS

Byrn et al. Pharmaceutical Solids: A Strategic Approach to Regulatory Considerations. Pharmaceutical Research 12(7):945-954 (1995).
Berge et al. Pharmaceutical Salts. Journal of Pharmaceutical Sciences 66(1):1-19 (Jan. 1977).
Chemical Abstracts Registry Entry 375362-97-3, entered Dec. 14, 2001.
Geis et al. Tricyclic theophylline derivatives with high water-solubility: structure-activity relationships at adenosine receptors, phosphodiesterases, and benzodiazepine binding sites. Pharmazie 50(5):333-336 (1995).
Haede et al., Herstellung Kondensierter 2-Alkylthio-4-hydroxypyrimidine J. Heterocyclic Chem. 18(7):1417-1419 (1981).
Haider et al., Product Class 9: Cinnolines in Science of Synthesis. ChemInform 16:251-313 (2004).
Katritzky et al., Polycyclic Heteroaromatics from Reactions of Acylbenzotriazoles with Aryl Isocyanates, J. Org. Chem., 65:8069-8073 (2000).
Landells et al. A biochemical and functional assessment of monocyte phosphodiesterase activity in healthy and asthmatic subjects. Pulm Pharmacol Ther 13(5):231-239 (2000).
Lewgowd et al., Determination of Lipophilicity, pKa Measurement and Action on the Central Nervous System of Some Pyrimido[5,4-c]quinolines Acta Poloniae Pharm., 62(4):271-281 (2005).
Lewgowd et al., Synthesis and cytotoxicity of new potential intercalators based on tricyclic systems of some pyrimido[5,4-c]cinnoline and pyrimido[5,4-c]quinoline derivatives. Part I Acta Poloniae Pharm., 62(2):105-110 (2005).

(Continued)

*Primary Examiner* — Brian E Mcdowell

(74) *Attorney, Agent, or Firm* — Choate, Hall & Stewart LLP

(57) ABSTRACT

The present disclosure relates to the compound trans-4-[1-(3-chlorophenyl)-7-methoxy-2,4-dioxo-pyrimido[5,4-c]quinolin-3-yl]cyclohexanecarboxylic acid, pharmaceutically acceptable salts, and use thereof as a therapeutic agent including treatment of inflammatory disorders.

5 Claims, No Drawings

(56) References Cited

OTHER PUBLICATIONS

Menon et al., Synthesis and Antimicrobial Properties of Pyrimido[5,4-c]cinolin-2,4(1H,3H)-diones J. Indian Chem. Soc., 72(10):731-733 (1995).
Nargund et al. Synthesis and antimicrobial and anti-inflammatory activities of substituted 2-mercapto-3-(N-aryl)pyrimido[5,4-c]cinnolin-4-(3H)-ones. J Pharm Sci 81(4):365-366 (1992).
PCT/US2009/031819 International Search Report and Written Opinion dated Mar. 25, 2009.
PCT/US2020/044410 International Search Report and Written Opinion dated Mar. 25, 2021.
PCT/US2021/043111 International Search Report and Written Opinion dated Nov. 5, 2021.
Peter et al. Inhibition of cyclooxygenase-2 prevents adverse effects induced by phosphodiesterase type 4 inhibitors in rats. Br J Pharmacol 162(2):415-427 (2011).
PubChem CID 5213595, create date, Oct. 7, 2005.
Reimund et al. Anti-TNF-alpha properties of new 9-benzyladenine derivatives with selective phosphodiesterase-4-inhibiting properties. Biochem Biophys Res Commun 288(2):427-434 (2001).
Shindo et al., Synthesis of Heterocyclic Compounds Isosterically Related to Pyrazolo[4,3-c]quinolines as Benzodiazepine Receptor Ligands. Heterocycles 29(5):899-912 (1989).
Spina. PDE4 inhibitors: current status. Br J Pharmacol155:308-315 (2008).
Stanczak et al., Comparison of pharmacophore cinnoline and quinoline systems on the basis of computer calculation and pharmacological screening of their condensed systems. Pharmazie 56(6):501-505 (2001).
Stanczak et al., Determination of the Lipophilicity of Pyrimido[5,4-c]quinoline Derivatives by Reversed-Phase Thin-Layer Chromatography. Part 1. Lipophilicity of Pyrimido[5,4-c]quinolin-4(3H)-ones and 1,2,3,4-Tetrahydropyrimido[5,4 -c]quinolin-2,4-diones. J. Planar Chromatography—Modern TLC 15(3):169-176 (2002).
Stanczak et al., Synthesis and biological activity of some 4-amino-3-cinnoline carboxylic acid derivatives. Pharmazie 53(3):156-161 (1998).
Sturton et al. Phosphodiesterase 4 inhibitors for the treatment of COPD. Chest 121(5 Suppl):192S-196S (2002).
Zahran et al. Synthesis of some pyrimidines and their benzo-derivatives via 6 pi-electron cyclization reactions. Afinidad 52(460:415-418 (1995).

QUINOLINE DERIVATIVES, PHARMACEUTICALLY ACCEPTABLE SALTS, AND METHODS OF USE THEREOF

FIELD OF THE INVENTION

The present invention relates to the compound trans-4-[1-(3-chlorophenyl)-7-methoxy-2,4-dioxo-pyrimido[5,4-c] quinolin-3-yl]cyclohexanecarboxylic acid, pharmaceutically acceptable salts, and use thereof as a therapeutic agent for the treatment of disorders mediated by TNF-alpha or PDE4.

BACKGROUND OF THE INVENTION

Tumor necrosis factor-alpha (TNF-α), also referred to as TNF, DIF, TNF-alpha, TNFA, and TNFSF2, is a cell-associated cytokine that is processed from a 26 kd precursor form to a 17 kd soluble form. TNF-α has been shown to be a primary mediator in humans and in animals of inflammation, fever, and acute phase responses, similar to those observed during acute infection and shock. Excess TNF-α has been shown to be lethal. There is now considerable evidence that blocking the effects of TNF-α by use of soluble TNF receptor or with specific neutralizing antibodies can be beneficial in a variety of circumstances including autoimmune diseases such as rheumatoid arthritis (RA), non-insulin dependent diabetes mellitus (NIDDM or Type II diabetes), and Crohn's disease.

Phosphodiesterases (PDEs) comprise a superfamily of enzymes responsible for the hydrolysis and inactivation of the secondary messengers cyclic adenosine monophosphate (cAMP) and cyclic guanosine monophosphate (cGMP). Different PDE families have been identified (PDE1, PDE2, PDE3, PDE4, etc.) which differ in substrate preference, catalytic activity, sensitivity to endogenous activators and inhibitors, and encoding genes.

The PDE4 isoenzyme family exhibits a high affinity for cyclic AMP but has weak affinity for cyclic GMP. Increased cyclic AMP levels caused by PDE4 inhibition are associated with the suppression of cell activation in a wide range of inflammatory and immune cells, including lymphocytes, macrophages, basophils, neutrophils, and eosinophils. Moreover, PDE4 inhibition decreases the release of the cytokine Tumor Necrosis Factor-alpha (TNF-α).

In view of these physiological effects, PDE4 inhibitors of varied chemical structures have been disclosed for the treatment of chronic and acute inflammatory diseases and of other pathological conditions, diseases and disorders known to be susceptible to amelioration by inhibition of PDE4.

PDE4 inhibitors are thought to be useful in the treatment and/or prophylaxis of a variety of diseases/conditions, especially inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder such as Alzheimer's disease), depression, or pain. Ulcerative colitis and/or Crohn's disease are collectively often referred to as inflammatory bowel disease.

Further, compounds which inhibit the production of TNF-α are believed useful in a wide variety of diseases and disorders through mechanism based therapeutic intervention. TNF-α inhibitors are believed useful for diseases including but not limited to viral, alcoholic, or drug-induced acute and fulminant hepatitis, hepatic steatosis, both alcoholic and non-alcoholic, viral and non-viral hepatitis, hepatic cirrhosis, autoimmune hepatitis, chronic active hepatitis, Wilson's disease, myasthenia gravis, idiopathic sprue, autoimmune inflammatory bowel disease, ulcerative colitis, Crohn's disease, inflammatory bowel diseases, endocrine ophthalmopathy, Grave's disease, sarcoidosis, primary biliary cirrhosis, pancreatitis, nephritis, endotoxin shock, septic shock, haemodynamic shock, sepsis syndrome, post ischemic reperfusion injury, malaria, mycobacterial infection, meningitis, psoriasis, asthma, chronic obstructive pulmonary disease (COPD), eosinophilia, congestive heart failure, fibrotic diseases, cystic fibrosis, pulmonary fibrosis, hepatic fibrosis, renal fibrosis, cachexia, graft rejection, rejection by transplantation, cancer, diseases involving angiogenesis, autoimmune diseases, ankylosing spondylitis, autoimmune encephalomyelitis, autoimmune hematological disorders, hemolytic anemia, aplastic anemia, pure red cell anemia, idiopathic thrombocytopenia, systemic lupus erythematosus (SLE), polychondritis, scleroderma, Wegener granulomatosis, dermatomyositis, Reiter's syndrome, non infection uveitis, autoimmune keratitis, keratoconjunctivitis sicca, vernal keratoconjunctivitis, interstitial lung fibrosis, psoriatic arthritis, psoriasis and other benign or malignant proliferative skin diseases, atopic dermatitis, urticaria, neurodegenerative disorders, Parkinson's disease, Alzheimer's disease, acute and chronic multiple sclerosis, cancer, viral infection such as SARS, MERS, or COVID-19, human immunodeficiency virus (HIV), cachexia, thrombosis, skin inflammatory diseases, osteoarthritis (OA), osteoporosis, RA, emphysema, chronic bronchiolitis, allergic rhinitis, radiation damage, hyperoxic alveolar injury, periodontal disease, non-insulin dependent diabetes mellitus (Type II diabetes), and insulin dependent diabetes mellitus (Juvenile or Type I diabetes).

PDE4 inhibitors may be a valuable therapeutic option to treat respiratory viral infections such as SARS, MERS, or COVID-19 treatment due to their unique mechanism of action, resulting to the upstream inhibition of multiple cytokine signaling pathways along with the regulation of the pro-inflammatory/anti-inflammatory balance. Furthermore, PDE4 inhibitors may specifically ameliorate airway and lung inflammation, and protect patients from associated acute lung injury and severe respiratory failure leading to intubation and high mortality.

Thus, there is continued need to identify and develop new compounds that inhibit PDE4 enzyme activity and/or production of TNF-alpha.

SUMMARY OF THE INVENTION

COMPOUND I and pharmaceutically acceptable salts thereof, their preparation, and their use as an inhibitor of PDE4 activity and in the treatment of various medical conditions are disclosed herein.

In one aspect, the present invention provides trans-4-[1-(3-chlorophenyl)-7-methoxy-2,4-dioxo-pyrimido[5,4-c]quinolin-3-yl]cyclohexanecarboxylic acid ("COMPOUND I") and pharmaceutically acceptable salts thereof. In an embodiment, the present invention provides COMPOUND I and the HCl salt thereof.

In another aspect, the present invention provides a pharmaceutical composition comprising COMPOUND I or a pharmaceutically acceptable salt thereof and a pharmaceutically acceptable carrier.

In another aspect, the present invention provides a method of making COMPOUND I or a pharmaceutically acceptable salt thereof.

In another aspect, the present invention provides a method of treatment of a disorder mediated by TNF-alpha or PDE4 comprising administering COMPOUND I or a pharmaceutically acceptable salt thereof to a subject in need thereof, or administering a pharmaceutical composition comprising COMPOUND I or a pharmaceutically acceptable salt thereof and a pharmaceutically acceptable carrier to a subject in need thereof. In an embodiment, the present invention provides a method of treating a disease selected from the group consisting of COPD, atopic dermatitis, psoriasis, IBD and Crohn's disease.

In another aspect, the present invention provides COMPOUND I or a pharmaceutically acceptable salt thereof for use in the manufacture of a medicament for the treatment of a disorder mediated by TNF-alpha or PDE4.

These and other aspects and embodiments of the present invention are described in greater detail below.

DETAILED DESCRIPTION

Definitions

As used herein, COMPOUND I or compound of Formula (I) refers to the compound with the structure as shown below:

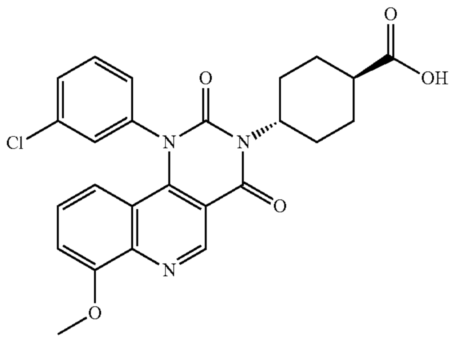 [SMILES: COc1cccc2c1ncc1c(=O)n([C@H]3CC[C@H](C(=O)O)CC3)c(=O)n(-c3cccc(Cl)c3)c12]

which may be identified as trans-4-[1-(3-chlorophenyl)-7-methoxy-2,4-dioxo-pyrimido[5,4-c]quinolin-3-yl]cyclohexanecarboxylic acid.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

The term "therapeutically effective amount" is used herein to denote the amount of COMPOUND I or a pharmaceutically acceptable salt thereof that will elicit the therapeutic response of a subject that is being sought. In an embodiment, the therapeutic response may be inhibiting PDE4 enzyme activity and/or inhibiting production of TNF-α in individual cells, tissues, organs of a subject. In an embodiment, a therapeutically effective amount may be achieved in a subject by administering a dosage of less than 1 gram or of less than 100 mg of compound per day. In another embodiment, the dosage level of administration is greater than 1 mg of compound per day. In an embodiment, the dosage of COMPOUND I or a pharmaceutically acceptable salt thereof administered is between 1 and 100 mg, or between 1 and 50 mg, or between 10 and 50 mg, or between 30 and 50 mg. In other embodiments, the dosage of COMPOUND I or a pharmaceutically acceptable salt thereof administered is between 1 and 20 mg, or between 5 and 15 mg, or between 10 and 20 mg, or between 20 and 30 mg.

The term "treatment" as used herein, refers to the full spectrum of treatments for a given condition or disorder from which a subject is suffering, including alleviation or amelioration of one or more of the symptoms resulting from that disorder, to the delaying of the onset or progression of the disorder.

The term "subject" may refer any mammal such as, but not limited to, humans. In one embodiment, the subject is a human. In another embodiment, the subject is a human who exhibits one or more symptoms characteristic of the condition to be treated. The term "subject" does not require one to have any particular status with respect to any hospital, clinic, or research facility (e.g., as an admitted patient, a study participant, or the like). In an embodiment, the subject may be "a subject in need thereof."

A "pharmaceutically acceptable carrier" is a medium generally accepted in the art for the delivery of biologically active agents to mammals, e.g., humans. Such carriers are generally formulated according to a number of factors well within the purview of those of ordinary skill in the art to determine and account for. These include, without limitation, the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., Remington's Pharmaceutical Sciences, 17th ed., Mack Publishing Company, Easton, Pa. 1985, the contents of which are incorporated herein by reference.

The term "pharmaceutically acceptable salt" refers to a salt prepared from pharmaceutically acceptable inorganic and organic acids and bases. For example, COMPOUND I may react with a number of inorganic and organic acids to form a pharmaceutically acceptable acid addition salt such as, but not limited to, hydrochloric, hydrobromic, hydroiodic, sulfuric, phosphoric, formic, acetic, propionic, citric, tartaric, and benzoic acids. Pharmaceutically acceptable base addition salts can be prepared from inorganic and organic bases. Salts derived from inorganic bases, include by way of example, sodium, potassium, lithium, ammonium, calcium and magnesium salts. Salts derived from organic bases include, but are not limited to, salts of primary, secondary and tertiary amines. Specific examples of such amines include, by way of example, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, choline, betaine, and ethylenediamine. Such pharmaceutically acceptable salts and common methodology for preparing them are well known in the art. See, for example, P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts", Journal of Pharmaceutical Sciences, Vol. 66, No. 1, January 1977.

1. Compounds

In one aspect, the present invention provides COMPOUND I or a pharmaceutically acceptable salt thereof. In an embodiment, the present invention provides COMPOUND I. In another embodiment, the present invention provides a pharmaceutically acceptable salt of COMPOUND I. In a further embodiment, the present invention provides an acid salt of COMPOUND I. In a further embodiment, the present invention provides an HCl acid salt of COMPOUND I.

In another aspect, the present invention provides the compound

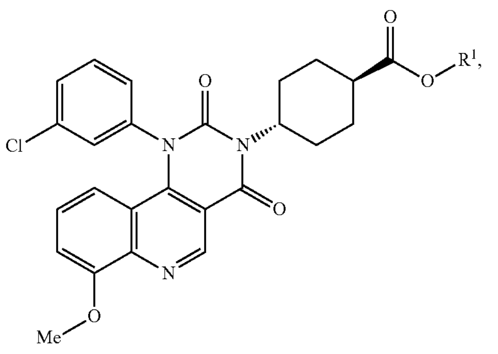

wherein $R^1$ is (C1-C6) alkyl optionally substituted one to 3 times with halogen. In an embodiment $R^1$ is methyl or tert-butyl.

2. Pharmaceutical Compositions

In another aspect, the present invention provides pharmaceutical compositions comprising COMPOUND I or a pharmaceutically acceptable salt thereof and a pharmaceutically acceptable carrier.

In an embodiment, the present invention provides a pharmaceutical composition comprising a COMPOUND I. In another embodiment, the present invention provides a pharmaceutical composition comprising a pharmaceutically acceptable salt of COMPOUND I. In a further embodiment, the present invention provides a pharmaceutical composition comprising an acid salt of COMPOUND I. In a further embodiment, the present invention provides a pharmaceutical composition comprising an HCl acid salt of COMPOUND I.

In another embodiment, the present invention provides pharmaceutical compositions of any of the previous embodiments, and further comprising one or more additional therapeutic agent(s). The one or more additional therapeutic agents are selected from steroids, cyclooxygenase inhibitors, non-steroidal-anti-inflammatory drugs, or TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, methotrexate, sulfasalazine, antilymphocytory immunoglobulines, antithymocytory immunoglobulines, azathioprine, cyclosporine, tacrolimus substances, ascomycin, rapamycin, or muromonab-CD3.

The present invention further provides pharmaceutical compositions of any of the previous embodiments comprising therapeutically effective amounts of COMPOUND I or a pharmaceutically acceptable salt thereof.

In accordance with another aspect of the invention there is also provided a process for the preparation of a pharmaceutical formulation comprising admixing COMPOUND I or a pharmaceutically acceptable salt thereof with one or more pharmaceutically acceptable carriers.

Pharmaceutical formulations may be presented in unit dose forms containing a predetermined amount of active ingredient per unit dose. Such a unit may contain, as a non-limiting example, 0.5 mg to 1 g of COMPOUND I or a pharmaceutically acceptable salt thereof, depending on the condition being treated, the route of administration, and the age, weight, and condition of the patient. Typical unit dosage formulations are those containing a daily dose or sub-dose, as herein above recited, or an appropriate fraction thereof, of an active ingredient. Such pharmaceutical formulations may be prepared by any of the methods well known in the pharmacy art.

In an embodiment, an individual dose form of a pharmaceutical composition may comprise COMPOUND I or a pharmaceutically acceptable salt thereof in an amount greater than 1 mg of COMPOUND I or pharmaceutically acceptable salt thereof. In another embodiment, the pharmaceutical composition may comprise COMPOUND I or a pharmaceutically acceptable salt thereof in an amount between 1 and 100 mg, or between 1 and 50 mg, or between 10 and 50 mg, or between 30 and 50 mg. In other embodiments, the pharmaceutical composition may comprise COMPOUND I or a pharmaceutically acceptable salt thereof in an amount between 1 and 20 mg, or between 5 and 15 mg, or between 10 and 20 mg, or between 20 and 30 mg.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful, certain routes will be preferable to others.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like.

Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Where appropriate, dosage unit formulations for oral administration can be microencapsulated. The formulation can also be prepared to prolong or sustain the release as for example by coating or embedding particulate material in polymers, wax or the like.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a nontoxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Suitable packaging for the pharmaceutical solution formulations may be all approved containers intended for parenteral use, such as plastic and glass containers, ready-to-use syringes and the like. In an embodiment, the container is a sealed glass container, such as a vial or an ampoule. A hermetically sealed glass vial is one example of a sealed glass container. According to an embodiment of the present invention, there is provided, in a sealed glass container, a sterile, injectable solution comprising COMPOUND I or a pharmaceutically acceptable salt thereof in a physiologically acceptable solvent, and which has an appropriate pH for stability. Acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide and the pH of the combined formulation administered is between pH 5.0 and 7.0. One or more additional components such as co-solubilizing agents, tonicity adjustment agents, stabilizing agents and preservatives, for instance of the kind previously specified, may be added to the solution prior to passing the solution through the sterilizing filter.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Further, the compositions of the present invention may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example. Pharmaceutical formulations adapted for rectal administration may be presented as suppositories or as enemas.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

3. Synthetic Methods

Methods for the preparation of COMPOUND I and the HCl salt thereof are described in the Examples section below.

In another aspect, the present invention provides a method for making COMPOUND I or a salt thereof, comprising hydrolyzing the compound

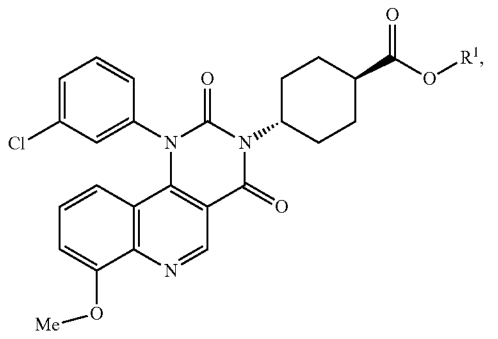

wherein $R^1$ is (C1-C6) alkyl optionally substituted one to 3 times with halogen. In an embodiment $R^1$ is methyl or tert-butyl. In another embodiment, $R^1$ is ethyl.

In another aspect, the present invention provides a method for making a pharmaceutically acceptable acid salt of COMPOUND I, comprising reacting COMPOUND I with a pharmaceutically acceptable acid in a suitable solvent. In an embodiment, the pharmaceutically acceptable acid is hydrochloric acid. In further embodiment, the COMPOUND I is reacted with hydrochloric acid to form HCl salts of COMPOUND I.

4. Methods of Treatment

In another aspect, the present invention provides a method of treatment comprising administering COMPOUND I or a pharmaceutically acceptable salt thereof to a subject in need thereof, or administering a pharmaceutical composition comprising COMPOUND I or a pharmaceutically acceptable salt thereof and a pharmaceutically acceptable carrier. In an embodiment, the method comprises administering a therapeutically effective amount of COMPOUND I or a pharmaceutically acceptable salt thereof.

A pharmaceutical composition of the present invention may be administered at a dosage level of less than 1 g of COMPOUND I or a pharmaceutically acceptable salt thereof per dose or per day. In another embodiment, the dosage level of administration is greater than 1 mg of COMPOUND I or a pharmaceutically acceptable salt thereof per dose or per day. The amount of active ingredient that may be combined with the carrier materials to produce a single dosage will vary depending upon the host treated and the particular mode of administration. For example, in one non-limiting embodiment, a dosage unit forms, such as a tablet or capsule, intended for oral administration to humans may contain less than 100 mg of COMPOUND I or pharmaceutically acceptable salt thereof with an appropriate and convenient amount of carrier material. In another embodiment, the dosage level of administration is greater than 1 mg of COMPOUND I or pharmaceutically acceptable salt thereof per day. In an embodiment, the dosage of COMPOUND I or a pharmaceutically acceptable salt thereof administered is between 1 and 100 mg, or between 1 and 50 mg, or between 10 and 50 mg, or between 30 and 50 mg. In other embodiments, the dosage of COMPOUND I or a pharmaceutically acceptable salt thereof administered is between 1 and 20 mg, or between 5 and 15 mg, or between 10 and 20 mg, or between 20 and 30 mg.

The dosage and/or the frequency of administration per day (once a day, twice a day, etc.) or per period (once a week, twice a week, etc.) may be individualized by the clinician based on the specific clinical condition of the subject being treated. Thus, it will be understood that the specific dosage level and frequency of administration for any particular subject may depend upon a variety of factors such as, but not limited to, the age, body weight, general health, sex, diet, time of administration, route of administration, rate of excretion, drug combination and the severity of the particular disease undergoing therapy.

Another embodiment of the present invention includes a method of inhibiting the activity of TNF-α in a subject in need thereof through the administration of COMPOUND I or a pharmaceutically acceptable salt thereof.

Another embodiment of the present invention includes a method of inhibiting PDE4 in a subject in need thereof through the administration of COMPOUND I or a pharmaceutically acceptable salt thereof.

Another embodiment of the present invention includes a method for the treatment of conditions or disorders mediated by activity of TNF-α through the administration of COMPOUND I or a pharmaceutically acceptable salt thereof.

Another embodiment of the present invention includes a method for the treatment of conditions or disorders mediated by PDE4 through the administration of COMPOUND I or a pharmaceutically acceptable salt thereof.

Another embodiment of the present invention includes a method for the treatment of an inflammatory disease through the administration of COMPOUND I or a pharmaceutically acceptable salt thereof. Inflammatory diseases may include, as non-limiting examples, viral, alcoholic, or drug-induced acute and fulminant hepatitis, hepatic steatosis, both alcoholic and non-alcoholic, viral and non-viral hepatitis, hepatic cirrhosis, autoimmune hepatitis, chronic active hepatitis, Wilson's disease, myasthenia gravis, idiopathic sprue, autoimmune inflammatory bowel disease, ulcerative colitis, Crohn's disease, inflammatory bowel diseases, endocrine ophthalmopathy, Grave's disease, sarcoidosis, primary biliary cirrhosis, pancreatitis, nephritis, endotoxin shock, septic shock, haemodynamic shock, sepsis syndrome, post ischemic reperfusion injury, malaria, mycobacterial infection, meningitis, psoriasis, asthma, chronic obstructive pulmonary disease (COPD), eosinophilia, congestive heart failure, fibrotic diseases, cystic fibrosis, pulmonary fibrosis, hepatic fibrosis, renal fibrosis, cachexia, graft rejection, graft vs. host disease, rejection by transplantation, cancer, diseases involving angiogenesis, autoimmune diseases, ankylosing spondylitis, autoimmune encephalomyelitis, autoimmune hematological disorders, hemolytic anemia, aplastic anemia, pure red cell anemia, idiopathic thrombocytopenia, systemic lupus erythematosus (SLE), polychondritis, scleroderma, Wegener granulomatosis, dermatomyositis, Reiter's syndrome, non infection uveitis, autoimmune keratitis, keratoconjunctivitis sicca, vernal keratoconjunctivitis, interstitial lung fibrosis, psoriatic arthritis, psoriasis and other benign or malignant proliferative skin diseases, atopic dermatitis, urticaria, neurodegenerative disorders, Parkinson's disease, Alzheimer's disease, acute and chronic multiple sclerosis, cancer, viral infection such as SARS, MERS, or COVID-19, human immunodeficiency virus (HIV), cachexia, thrombosis, skin inflammatory diseases, osteoarthritis (OA), osteoporosis, RA, emphysema, chronic bronchiolitis, allergic rhinitis, radiation damage, hyperoxic alveolar injury, periodontal disease, non-insulin dependent diabetes mellitus (Type II diabetes), and insulin dependent diabetes mellitus (Juvenile or Type I diabetes).

In another embodiment, such treatment relates to conditions mediated by the inhibition of PDE4. Such conditions include a variety of conditions, especially inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder such as Alzheimer's disease), depression, or pain. Ulcerative colitis and/or Crohn's disease are collectively often referred to as inflammatory bowel disease.

In an embodiment of the present invention, the inflammatory and/or allergic disease is chronic obstructive pulmonary disease (COPD), asthma, psoriasis, or rheumatoid arthritis in a mammal (e.g. human). In another embodiment, the present invention provides a method of treating a disease selected from the group consisting of COPD, atopic dermatitis, psoriasis, IBD and Crohn's disease.

The compounds of the present invention may also be administered in combination with other conventional anti-inflammatory or immunosuppressive agents, such as steroids, cyclooxygenase inhibitors, non-steroidal-anti-inflammatory drugs, TNF-α antibodies or other TNF-binding proteins, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, methotrexate, sulfasalazine, antilymphocyte immunoglobulins, antithymocyte immunoglobulins, azathioprine, cyclosporine, tacrolimus substances, ascomycin, rapamycin, adalimumab, muromonab-CD3 or other antibodies or fusion proteins that modulate T-cell function such as abatacept, alefacept and efalizumab.

As noted above, the compounds of the present invention may be employed alone or in combination with other therapeutic agents. Such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the formulae of the present invention including salts thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be dose in time or remote in time. The compounds of the present invention may be used in the treatment of a variety of disorders and conditions and, as such, the compounds of the present invention may be used in combination with a variety of other suitable therapeutic agents useful in the treatment or prophylaxis of those disorders or conditions.

5. Use in Method of Manufacture of Medicament

In another aspect, present invention provides the use of COMPOUND I or a pharmaceutically acceptable salt thereof in the manufacture of a medicament for use in the treatment of an inflammatory disease. Inflammatory diseases may include, as non-limiting examples, viral, alcoholic, or drug-induced acute and fulminant hepatitis, hepatic steatosis, both alcoholic and non-alcoholic, viral and non-viral hepatitis, hepatic cirrhosis, autoimmune hepatitis, chronic active hepatitis, Wilson's disease, myasthenia gravis, idiopathic sprue, autoimmune inflammatory bowel disease, ulcerative colitis, Crohn's disease, inflammatory bowel diseases, endocrine ophthalmopathy, Grave's disease, sarcoidosis, primary biliary cirrhosis, pancreatitis, nephritis, endotoxin shock, septic shock, haemodynamic shock, sepsis syndrome, post ischemic reperfusion injury, malaria, mycobacterial infection, meningitis, psoriasis, asthma, chronic obstructive pulmonary disease (COPD), eosinophilia, congestive heart failure, fibrotic diseases, cystic fibrosis, pulmonary fibrosis, hepatic fibrosis, renal fibrosis, cachexia, graft rejection, graft vs. host disease, rejection by transplantation, cancer, diseases involving angiogenesis, autoimmune diseases, ankylosing spondylitis, autoimmune encephalomyelitis, autoimmune hematological disorders, hemolytic anemia, aplastic anemia, pure red cell anemia, idiopathic thrombocytopenia, systemic lupus erythematosus (SLE), polychondritis, scleroderma, Wegener granulomatosis, dermatomyositis, Reiter's syndrome, non infection uveitis, autoimmune keratitis, keratoconjunctivitis sicca, vernal keratoconjunctivitis, interstitial lung fibrosis, psoriatic arthritis, psoriasis and other benign or malignant proliferative skin diseases, atopic dermatitis, urticaria, neurodegenerative disorders, Parkinson's disease, Alzheimer's disease, acute and chronic multiple sclerosis, cancer, viral infection such as SARS, MERS, or COVID-19, human immunodeficiency virus (HIV), cachexia, thrombosis, skin inflammatory diseases, osteoarthritis (OA), osteoporosis, RA, emphysema, chronic bronchiolitis, allergic rhinitis, radiation damage, hyperoxic alveolar injury, periodontal disease, non-insulin dependent diabetes mellitus (Type II diabetes), and insulin dependent diabetes mellitus (Juvenile or Type I diabetes).

In another embodiment, present invention provides the use of COMPOUND I or a pharmaceutically acceptable salt thereof in the manufacture of a medicament for use in treatment of inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder such as Alzheimer's disease), depression, or pain. Ulcerative colitis and/or Crohn's disease are collectively often referred to as inflammatory bowel disease. In one embodiment, the inflammatory and/or allergic disease is chronic obstructive pulmonary disease (COPD), asthma, rheumatoid arthritis or allergic rhinitis in a mammal (e.g. human).

COMPOUND I or a pharmaceutically acceptable salt thereof may be used in the manufacture of a medicament in combination with other conventional anti-inflammatory or immunosuppressive agents, such as steroids, cyclooxygenase inhibitors, non-steroidal-anti-inflammatory drugs, TNF-α antibodies or other TNF-binding proteins, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, methotrexate, sulfasalazine, antilymphocyte immunoglobulins, antithymocyte immunoglobulins, azathioprine, cyclosporine, tacrolimus substances, ascomycin, rapamycin, adalimumab, muromonab-CD3 or other antibodies or fusion proteins that modulate T-cell function such as abatacept, alefacept and efalizumab.

Another embodiment of the present invention includes a use of COMPOUND I or a pharmaceutically acceptable salt thereof in the manufacture of a medicament for use in inhibiting the activity of TNF-α in a subject in need thereof.

Another embodiment of the present invention includes a use of COMPOUND I or a pharmaceutically acceptable salt thereof in the manufacture of a medicament for use in inhibiting PDE4 in a subject in need thereof.

Another embodiment of the present invention includes a use of COMPOUND I or a pharmaceutically acceptable salt thereof in the manufacture of a medicament for use in the treatment of conditions or disorders mediated by activity of TNF-α.

Another embodiment of the present invention includes a use of COMPOUND I or a pharmaceutically acceptable salt thereof in the manufacture of a medicament for use in the treatment of conditions or disorders mediated by PDE4.

Examples

Synthesis of Compound I and HCl Salt Thereof

Step 1:

A 40 mL reaction vial was charged with ethyl-4-chloro-8-methoxyquinoline-3-carboxylate (1.25 g, 4.7 mmol), m-chloroaniline (0.69 g, 5.4 mmol, 1.15 eq), 1-butanol (10 mL) and acetic acid (0.3 mL). The mixture stirred at 95° C. for 5 hr and IPC LCMS indicated the reaction was complete. The 1-butanol was removed under vacuum and the mixture diluted with ethyl acetate (75 mL). The organic layer was washed with saturated sodium bicarbonate aqueous solution (25 mL) and concentrated to dryness. The residue was purified by flash column chromatography eluting with DCM/ethyl acetate (1:0 to 1:1) to give ester intermediate ethyl 4-(3-chloroanilino)-8-methoxy-quinoline-3-carboxylate (1.05 g). 62% yield. LCMS n/e 357.1 $(M+1)^+$; $^1$H NMR, 300 MHz ($CDCl_3$) δ 1.45 (t, 3H), 4.08 (s, 3H), 4.44 (q, 2H), 6.84 (br d, 1H), 6.99 (t, 1H), 7.04 (dd, 1H), 7.05 (d, 1H), 7.16 (t, 1H), 7.20 s, 1H), 7.22 (dd, 1H), 9.29 (s, 1H), 10.25 (s, 1H) ppm.

Step 2:

A 250 mL round bottom flask was charged with the ester from Step 1 (1.05 g, 2.94 mmol), THF/MeOH (40 mL, 1:1), 4 N aq NaOH (3 mL, 12.0 mmol) and water (17 mL). The reaction stirred at 60° C. for 1.0 hr and IPC LCMS indicated the reaction was complete. The mixture was concentrated to dryness, acidified with 2N HCl (8 mL) and diluted with water (50 mL). The slurry was filtered, and the wet cake was washed with water. The solids were dried for 18 hr to provide step 2 acid, 4-(3-chloroanilino)-8-methoxy-quinoline-3-carboxylic acid (0.77 g), 79% yield. Note: a drop of 37% HCl was added for NMR and LCMS analysis.

LCMS m/e 329.0 $(M+1)^+$; $^1$H NMR, 300 MHz ($d_6$-DMSO) δ 4.10 (s, 3H), 7.34 (m, 1H), 7.40 (m, 1H), 7.45 (d, 1H), 7.52 (m, 1H), 7.76 (m, 1H), 7.77 (s, 1H), 7.78 (dd, 1H), 8.80 (s, 1H), 11.78 (s, 1H) ppm (COOH proton not visible).

Step 3:

A 40 mL reaction vial was charged with the acid from Step 2 (0.73 g, 2.22 mmol), EDC-HCl (0.64 g, 3.33 mmol 1.5 eq), HOBt (0.45 g, 3.33 mmol. 1.5 eq), 4-dimethylamino pyridine (DMAP) (0.41 g, 3.33 mmol, 1.5 eq) and anhydrous DMF (9 mL). The slurry was stirred at 25° C. for 30 min and tert-butyl trans-4-aminocyclohexane-1-carboxylate (0.84 g, 4.21 mmol, 1.9 eq) was added. The was mixture stirred at 25° C. for 3 hr. IPC analysis by LCMS after 3 hr showed 16% k conversion. The mixture was stirred at 37° C. for 24 hr. After IPC analysis showed 97% conversion, the reaction was diluted with ethyl acetate (75 nil) and washed with brine (3×25 mL). The organic layer was concentrated to dryness. The residue was purified by flash column chromatography on silica gel eluting with ethyl acetate/methanol (100/0 to 100/10) to give Amide I shown below (0.96 g), 84% yield.

LCMS m/e 510.2 $(M)^+$; $^1$H NMR, 300 MHz ($CDCl_3$) δ 1.24 (m, 2H), 1.34 (m, 2H) 1.44 (s, 9H), 1.57 (m, 3H), 2.05 (br d, 1H), 2.17 (m, 1H), 3.97 (m, 1H), 4.08 (s, 3H), 6.13 (br d, 1H), 6.80 (d, 1H), 6.89 (t, 1H), 7.02 (m, 2H), 7.14 (t, 1H), 7.25 (m, 2H), 8.84 (s, 1H), 10.14 (s, 1H) ppm.

Amide 1

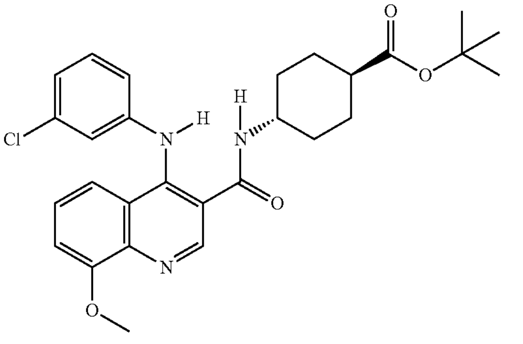

Step 4:

A 40 mL reaction vial was charged with the Amide 1 from Step 3 (510 mg, 1.0 mmol), 4-nitrophenyl chloroformate (605 mg, 3.0 mmol, 3.0 eq), DMAP (489 mg, 4.0 mmol, 4.0 eq) and NMP (5 mL). The mixture was stirred at 95° C. for 18 hr and IPC LCMS after 18 hr showed 90% conversion. The reaction mixture was diluted with ethyl acetate (75 ml) and washed with water (35 mL) and brine (2×35 mL). The organic layer was concentrated to dryness. The residue was purified by flash column chromatography on silica gel eluting with heptane/ethyl acetate (3:1 to 1:1) to give cyclic urea 1 shown below (350 mg), 65.3% yield.

LCMS m/e 536.2 $(M)^+$; $^1H$ NMR, 300 MHz ($CDCl_3$) S 1.45 (s, 9H), 1.56 (qd, 2H)·1.83 (br d, 2H), 2.10 (br d, 2H), 2.25 (tt, 1H), 2.54 (qd, 2H), 4.07 (s, 3H), 4.92 (tt, 1H), 6.48 (dd, 1H), 7.06 (dd, 1H) 7.10 (t, 1H), 7.24 (dd, 1H), 7.39 (t, 1H), 7.50 (t, 1H), 7.54 (ddd, 1H), 9.54 (s, 1H) ppm.

Cyclic Urea 1

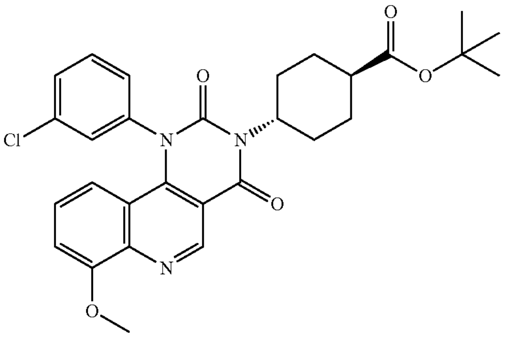

Step 5:

A 40 mL reaction vial was charged with cyclic urea 1 from the previous step (350 mg), AcOH (20 mL) and 6 N HCl (10 mL). The reaction was stirred at 20° C. for 18 hr, IPC LCMS at 18 hr showed that the reaction was complete. The reaction was diluted with water (20 mL) and DCM (75 mL) and the layers separated. The organic layer was concentrated to dryness. The residue was slurried with ethyl acetate (25 mL). The slurry was filtered. The collected solid was washed with heptane and dried in vacuum oven for 24 hr under nitrogen stream to give 220 mg of Compound I, 70% yield.

LCMS m/e 480.1 $(M+1)^+$:

$^1H$ NMR, 300 MHz ($CDCl_3$) δ 1.64 (dt, 2H), 1.88 (br d, 2H), 2.20 (br d, 2H), 2.42 (tt, 1H), 2.58 (dt, 2H), 4.07 (s, 3H), 4.95 (br t, 1H), 6.48 (dd, 1H), 7.07 (dd, 1H), 7.11 (t, 1H), 7.26 (m, 1H), 7.40 (t, 1H), 7.48 (t, 1H) 7.54 (d, 1H), 9.55 (s, 1H) ppm (COOH and HCl protons not visible).

$^1H$ NMR, 300 MHz ($d_6$-DMSO) δ 1.44 (hr dd, 2H), 1.79 (br d, 2H), 2.04 (hr d, 2H), 2.20 (br t, 1H) 2.40 (br dd, 2H), 3.96 (s, 3H), 4.1 (br, water and/or HCl and/or COOH), 4.74 (br tt, 1H), 6.37 (d, 1H), 7.20 (t, 1H), 7.27 (d, 1H), 7.52 (dt, 1H), 7.61 (t, 1H), 7.67 (apparent s, 1H), 7.68 (apparent d, 1H), 9.27 (s, 1H) ppm.

PDE4 Inhibition Assays

A PDE4B2 fluorescence polarization assay kit (Catalog #60343) and a PDE4D7 TR-FRET assay kit (Catalog #60708) from BPS BioSciences™ were used to screen the HCl salt of COMPOUND I for inhibition of the PDE4B2 and PDE4D7 enzymes.

According to BPS BioSciences product information, the PDE4B2 fluorescence polarization assay kit assay is based on the binding of a fluorescent nucleotide monophosphate generated by PDE4B2 to the binding agent. Phosphodiesterases catalyze the hydrolysis of the phosphodiester bond in dye-labeled cyclic monophosphates. Beads selectively bind the phosphate group in the nucleotide product. This increases the size of the nucleotide relative to unreacted cyclic monophosphate. In the polarization assay, dye molecules with absorption transition vectors parallel to the linearly polarized excitation light are selectively excited. Dyes attached to the rapidly-rotating cyclic monophosphates will obtain random orientations and emit light with low polarization. Dyes attached to the slowly-rotating nucleotide-bead complexes will not have time to reorient and therefore will emit highly polarized light.

According to BPS Biosciences product information, the PDE4D7 TR-FRET assay is designed for identification of inhibitors of PDE4D7 using TR-FRET (Time Resolved Fluorescence Resonance Energy Transfer) technology. The assay is based on the generation of FAM-labeled nucleotide monophosphates by the phosphodiesterase. These phosphate groups bind to terbium-labeled nanoparticles, resulting in energy transfer from the terbium to the FAM, which emits a fluorescent signal at 520 nm. The change in fluorescent intensity can be easily measured using a fluorescence plate reader.

PDE4B2 Fluorescence Polarization Assay

The general assay protocol for PDE4B2 fluorescence polarization assay used to obtain the experimental data described below includes two steps: First, fluorescently labeled cAMP is incubated with a sample containing PDE4B2 for 1 hour. Second, a binding agent is added to the reaction mix to produce a change in fluorescent polarization that can then be measured using a fluorescence reader equipped for the measurement of fluorescence polarization. A detailed protocol is as follows:

Step 1: Dilute 20 µM FAM-Cyclic-3',5'-AMP stock 100-fold with PDE buffer to make a 200 nM solution. Make only sufficient quantity needed for the assay; store remaining 20 µM stock solution in aliquots at −20° C. Add 25 µl of FAM-Cyclic-3',5'-AMP (200 nM) to each well designated "Positive Control", "Test Inhibitor", and "Substrate Control". Add 20 µl of PDE assay buffer to each well designated "Substrate Control" and 45 µl of PDE assay buffer to each well designated "Blank". Add 5 µl of inhibitor solution to each well designated "Test Inhibitor". For the wells labeled "Positive Control", "Substrate Control" and "Blank", add 5 µl of the same solution without inhibitor (inhibitor buffer). Thaw PDE4B2 on ice. Upon first thaw, briefly spin tube containing enzyme to recover the full contents of the tube. Aliquot PDE4B2 enzyme into single-use aliquots. Store remaining undiluted enzyme in aliquots at −70° C. immediately. Note: PDE4B2 is very sensitive to freeze/thaw cycles. Dilute PDE4B2 in PDE buffer to 7.5 pg/μl (0.15 ng/reaction)*. Initiate reaction by adding 20 μl of PDE4B2 (7.5 pg/μl) to the wells designated "Positive Control" and "Test Inhibitor."

*Note: Optimal enzyme concentration may vary with the specific activity of the enzyme. Incubate at room temperature for 1 hour.

Step 2: Mix binding agent thoroughly and dilute binding agent 1:100 with binding agent diluent. Add 100 μl diluted binding agent to each microwell. Incubate at room temperature for 1 hour with slow shaking. Read the fluorescent polarization of the sample in a microtiter-plate reader equipped for the measurement of fluorescence polarization, capable of excitation at wavelengths ranging from 485 f 5 nm and detection of emitted light ranging from 528 f 10 nm. Blank value is subtracted from all other values.

PDE4D7 TR-FRET Assay

The general assay protocol for PDE4D7 TR-FRET assay used to obtain the experimental data described below includes two steps: First, the fluorescent-labeled cAMP is incubated with a sample containing PDE4D7 for 1 hour. Second, a binding agent and a terbium donor are added to the reaction mix and incubated for 1 hour. Then, fluorescence intensity can be measured using a fluorescence reader. A detailed protocol is as follows Step 1: Dilute 20 μM FAM-Cyclic-3',5'-AMP substrate stock solution 100-fold with PDE buffer to make a 200 nM solution. Make only a sufficient quantity needed for the assay; store remaining stock solution in aliquots at −20° C. Add 25 μl of FAM-Cyclic-3',5'-AMP (200 nM) to each well designated "Substrate Control", "Positive Control", and "Test Inhibitor". Add 25 μl of PDE assay buffer to each well designated "Tb-only Control". Add 5 μl of inhibitor solution to each well designated "Test Inhibitor". Add 5 μl of the same solution without inhibitor (inhibitor buffer) to the "Tb-only Control", "Substrate Control" and "Positive Control". Thaw PDE4D7 on ice. Upon first thaw, briefly spin tube containing enzyme to recover the full contents of the tube. Aliquot PDE4D7 enzyme into single-use aliquots. Store remaining undiluted enzyme in aliquots at −80° C. immediately. Dilute PDE4D7 in PDE buffer to 5 pg/μl (100 pg/reaction) in PDE buffer*. Add 20 μl of PDE assay buffer to the wells designated as the "Tb-only Control" and "Substrate Control". Initiate reaction by adding 20 μl of PDE4D7 (5 pg/μl) to the wells designated for the "Positive Control" and "Test Inhibitor".

*Note: optimal enzyme concentration may vary with the specific activity of the enzyme.

Step 2: Make binding dilution buffer by mixing equal volumes of Binding buffer A and Binding buffer B. For example, mix 1 ml Binding buffer A with 1 ml Binding buffer B. Mix binding agent thoroughly and dilute binding agent 1:50 with binding dilution buffer made in Step 1. Add Tb donor (1:1,000 dilution) to the mixture in Step 2. Add 100 μl to each well. Incubate at room temperature for 1 hour with slow shaking. Read the fluorescent intensity in a microtiter-plate reader capable of TR-FRET.

The data below was obtained using the screening procedures described above with various batches of COMPOUND I*HCl. Apremilast, a known inhibitor of PDE4, was used was also screened.

| Sample | PDE4B2 IC50 (nM) | PDE4D7 IC50 (nM) |
|---|---|---|
| COMPOUND I * HCI (Batch 1) | 1.9 | 1.5 |
| COMPOUND I * HCI (Batch 2) | 5.9 | 3.3 |
| COMPOUND I * HCI (Batch 3) | 1.3 | 1.1 |
| Apremilast | 9.8 | 7.6 |

What is claimed is:

1. A compound having the Formula (I):

(I)

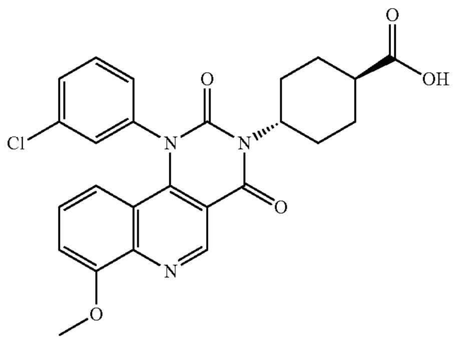

or a pharmaceutically acceptable salt thereof.

2. The compound of claim 1, wherein the compound is a compound of Formula (I).

3. The compound of claim 1, wherein the compound is an acid salt of the compound of Formula (I).

4. The compound of claim 3, wherein the compound is an HCl salt of the compound of Formula (I).

5. A pharmaceutical composition comprising a compound of claim 1, or a pharmaceutically acceptable salt thereof and a pharmaceutically acceptable carrier.

* * * * *